United States Patent
Jara Blazquez et al.

(10) Patent No.: US 10,359,278 B2
(45) Date of Patent: Jul. 23, 2019

(54) METHOD FOR MEASURING THICKNESS OF CARBON FIBER COMPONENTS USING ULTRASOUNDS

(71) Applicant: AIRBUS OPERATIONS, S.L., Getafe (ES)

(72) Inventors: Luis Jara Blazquez, Getafe (ES); David Torres Macarrilla, Getafe (ES); Sergio Bermejo Gonzalez, Getafe (ES); David Lopez Bravo, Getafe (ES)

(73) Assignee: Airbus Operations, S.L., Getafe (Madrid) (ES)

( * ) Notice: Subject to any disclaimer, the term of this patent is extended or adjusted under 35 U.S.C. 154(b) by 258 days.

(21) Appl. No.: 15/216,852

(22) Filed: Jul. 22, 2016

(65) Prior Publication Data
US 2017/0023360 A1    Jan. 26, 2017

(30) Foreign Application Priority Data
Jul. 24, 2015 (EP) .................................... 15382384

(51) Int. Cl.
*G01B 17/02* (2006.01)
*G01N 29/07* (2006.01)
*G01N 29/30* (2006.01)

(52) U.S. Cl.
CPC .............. *G01B 17/02* (2013.01); *G01N 29/07* (2013.01); *G01N 29/30* (2013.01);
(Continued)

(58) Field of Classification Search
CPC ........ G01B 17/02; G01B 17/00; G01B 17/06; G01N 29/07; G01N 29/30;
(Continued)

(56) References Cited

U.S. PATENT DOCUMENTS

| | | | |
|---|---|---|---|
| 5,163,027 A | * | 11/1992 | Miller .................... G01B 3/30 367/13 |
| 5,448,915 A | | 9/1995 | Dunn et al. |

(Continued)

FOREIGN PATENT DOCUMENTS

JP    S58169016 A    10/1983

OTHER PUBLICATIONS

D.W. Schindel and D.A. Hutchins, Through thickness characterization of solids by wideband air-coupled ultrasound, Ultrasonics 1995 vol. 33 No. 1, pp. 11-17.

(Continued)

*Primary Examiner* — Justin Seo
*Assistant Examiner* — Rose M Miller
(74) *Attorney, Agent, or Firm* — John S. Artz; Dickinson Wright PLLC

(57) ABSTRACT

The present disclosure refers to a method for measuring thickness in any type of carbon fiber component, even in components having parts with different thickness and integrating at least a second material. The method includes measuring with the maximum and minimum real thickness of the component, and measuring with ultrasonic equipment the time that the ultrasound takes to propagate across the component part with maximum and with minimum thickness, calculating a thickness correction value, and calculating an ultrasound test speed from said thickness correction value, said measured times, and said measured maximum and minimum real thickness. Then, the total thickness of each of the parts of the component are measured, using ultrasounds with the same calculated ultrasound test speed, and the thickness correction value is applied to each of the measuring total thickness of each part, to determine a corrected carbon fiber thickness for each part.

5 Claims, 3 Drawing Sheets

(52) U.S. Cl.
CPC .......... *G01N 2291/011* (2013.01); *G01N 2291/0231* (2013.01); *G01N 2291/0235* (2013.01); *G01N 2291/02854* (2013.01)

(58) Field of Classification Search
CPC ..... G01N 2291/011; G01N 2291/0231; G01N 2291/0235; G01N 2291/02854
USPC .................. 73/597, 598, 1.81, 1.86, 1.82
See application file for complete search history.

(56) References Cited

U.S. PATENT DOCUMENTS

| | | | |
|---|---|---|---|
| 7,762,120 B2* | 7/2010 | Vaccaro | G01N 29/30 73/1.86 |
| 2005/0092091 A1* | 5/2005 | Greelish | G01N 29/0609 73/617 |
| 2006/0213250 A1* | 9/2006 | Vaccaro | G01N 29/30 73/1.86 |
| 2011/0232360 A1 | 9/2011 | Deangelo et al. | |
| 2016/0113634 A1* | 4/2016 | Kim | A61B 8/587 702/97 |
| 2016/0209375 A1* | 7/2016 | Yamaoka | G01N 29/04 |

OTHER PUBLICATIONS

European Search Report, dated Jan. 28, 2016, 6 Pages.

\* cited by examiner

|         | Measure by UT |                   |                     |                      |                |               |
|---------|---------------|-------------------|---------------------|----------------------|----------------|---------------|
| Caliper | Time=E/V      | Correction factor | Calculated velocity | Calculated thickness | Accuracy, mm   | Accuracy %    |
| 17.92   | 0.006106529   | 0.126             | 2955                | 17.920               | 0.000          | 0.00          |
| 16.06   | 0.005491409   | 0.126             | 2955                | 16.102               | -0.042         | -0.26         |
| 16.08   | 0.005484536   | 0.126             | 2955                | 16.082               | -0.002         | -0.01         |
| 16.00   | 0.005450172   | 0.126             | 2955                | 15.980               | 0.020          | 0.12          |
| 14.08   | 0.004814433   | 0.126             | 2955                | 14.102               | -0.022         | -0.15         |
| 13.96   | 0.004769759   | 0.126             | 2955                | 13.970               | -0.010         | -0.07         |
| 12.08   | 0.004130584   | 0.126             | 2955                | 12.081               | -0.001         | -0.01         |
| 12.04   | 0.004109966   | 0.126             | 2955                | 12.020               | 0.020          | 0.17          |
| 10.06   | 0.003443299   | 0.126             | 2955                | 10.050               | 0.010          | 0.10          |
| 10.02   | 0.003439863   | 0.126             | 2955                | 10.040               | -0.020         | -0.20         |
| 8.24    | 0.002828179   | 0.126             | 2955                | 8.232                | 0.008          | 0.10          |
| 8.04    | 0.002776632   | 0.126             | 2955                | 8.080                | -0.040         | -0.49         |
| 6.28    | 0.002178694   | 0.126             | 2955                | 6.313                | -0.033         | -0.52         |
| 6.04    | 0.002092784   | 0.126             | 2955                | 6.059                | -0.019         | -0.31         |
| 4.22    | 0.001477663   | 0.126             | 2955                | 4.241                | -0.021         | -0.50         |
| 2.20    | 0.000786942   | 0.126             | 2955                | 2.200                | 0.000          | 0.00          |

FIG. 4

METHOD FOR MEASURING THICKNESS OF CARBON FIBER COMPONENTS USING ULTRASOUNDS

CROSS-REFERENCE TO RELATED APPLICATIONS

The present disclosure claims priority to European Application No. 15382384.4 filed on Jul. 24, 2015, which is hereby incorporated by reference, as though set forth fully herein.

FIELD OF DISCLOSURE

The present disclosure refers in general to ultrasonic testing techniques for quality dimensional measurements.

More specifically, the present disclosure refers to a method for measuring thickness using ultrasounds in carbon fiber based components.

An object of the present disclosure is to provide thickness measuring methods with enhanced accuracy and simplicity, and which can be applied to heterogeneous composite components formed by several types of materials.

BACKGROUND OF THE DISCLOSURE

It is known that ultrasonic measurements provide the thickness of a component by measuring the time (T) that an ultrasonic signal takes to propagate across a component (1) and return to the ultrasound equipment (2). FIG. 1 shows this technique, wherein the thickness of the component (E) is calculated by the formula $E = V \cdot T/2$, wherein (V) is the ultrasound speed set at the ultrasound emitter (2).

Since the measurement accuracy of each ultrasound speed is different for different thickness to be measured, standard use of ultrasonic automatic equipment for measuring the thickness of a component having areas of different thickness, conventionally requires several adjustments of the generated ultrasonic speed (V) for maximum and minimum thickness of that particular component, in order to select a ultrasonic speed which provides an acceptable accuracy for each thickness range. Due to these readjustments, the measurement process is slow and complex.

Additionally, some aircraft components like wings skin covers, are typically formed by several layers of different materials, like carbon fiber, copper mesh, adhesive layers, excess of resin, etc., so that the total thickness of the component in a specific area, is the carbon fiber thickness plus the thickness of the other materials.

Since ultrasound propagation speed changes for each type of material (see FIG. 2), the lack of homogeneity of these components, the surface roughness, in addition to the different thicknesses of the component, causes that the accuracy required for dimensional measurements, is not guaranteed. Currently, the error caused by the additional materials different than carbon fiber is disregarded.

SUMMARY OF THE DISCLOSURE

The present disclosure is defined in the attached independent claim and it overcomes the above-mentioned drawbacks of the prior art, by providing an automatic method for measuring thickness of heterogeneous components in which carbon fiber is the main component with variable thickness and it additionally integrates at least a second material different with constant thickness, like a copper mesh, adhesive layers, fiber glass, etc.

According to the present disclosure, an unique ultrasound speed is calculated throughout all of the component and corresponding to the material of variable thickness, capable of accurately measuring the thickness of the carbon fiber, but fails due to the different propagation speed of the second material and disturbance caused by the surface roughness. As both the thickness of the second material and surface roughness are constant in all areas, so the error obtained is constant too, and the calculation of this error allows to apply a precise correction on the results.

The method includes the steps of measuring the maximum and minimum real thickness of the component, that is, measurement of the real thickness of the thicker part and the real thickness of the thinner part of the component. These measurements are carried out conventionally by a mechanical thickness measurement device, such as a calipper or a micrometer for example (or any another way in order to know the real thickness).

Then, an automatic ultrasound equipment is used to measure the time between when the signal is output until the echo is received after bouncing at the bottom of each thickness part measured with micrometer in the previously step.

By the real value of the maximum and minimum thickness and the time spent by the signal in crossing them, we can propose an equation that allows us to calculate the ultrasound test speed and the thickness correction factor.

Then, the automatic ultrasound measurement equipment is set at the calculated ultrasound test speed, and the total thickness measurements are taken through an entire component using the same calculated ultrasound test speed.

Finally, the calculated thickness correction value is applied to each of the measuring total thickness for each part of the component, to determine a corrected carbon fiber thickness for each part.

Some advantages of the present disclosure are the followings:

Since only one speed setting is needed at the beginning of the process, the measuring process is greatly simplified.

Improved accuracy. In the range of 0-18 mm of thickness in calibration block, the method of the present disclosure provides a maximum of +0.02 mm/−0.04 mm of uncertainty in the measurement. Existing methods without readjustment provides in the same range and calibration block +0.09 mm/−0.15 mm of uncertainty.

BRIEF DESCRIPTION OF THE FIGURES

Preferred embodiments of the present disclosure, are henceforth described with reference to the accompanying drawings, wherein:

FIG. 4 is a table containing an example of calculated and measured data to demonstrate the accuracy of the carbon fiber measurement method in accordance with an aspect of the present disclosure.

DETAILED DESCRIPTION OF THE PRESENT DISCLOSURE

Figure 1:
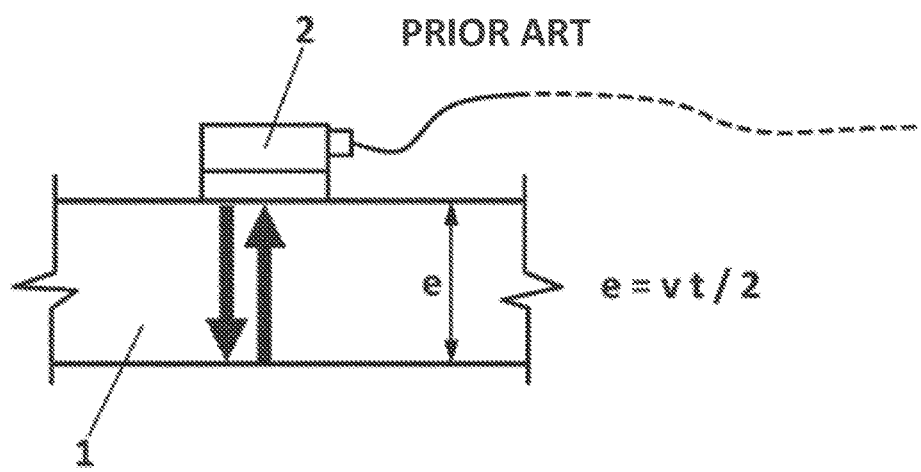
FIG. 1 is an illustration of a schematic representation of the prior art traditional process for thickness measurement using ultrasounds.
Figure 2:
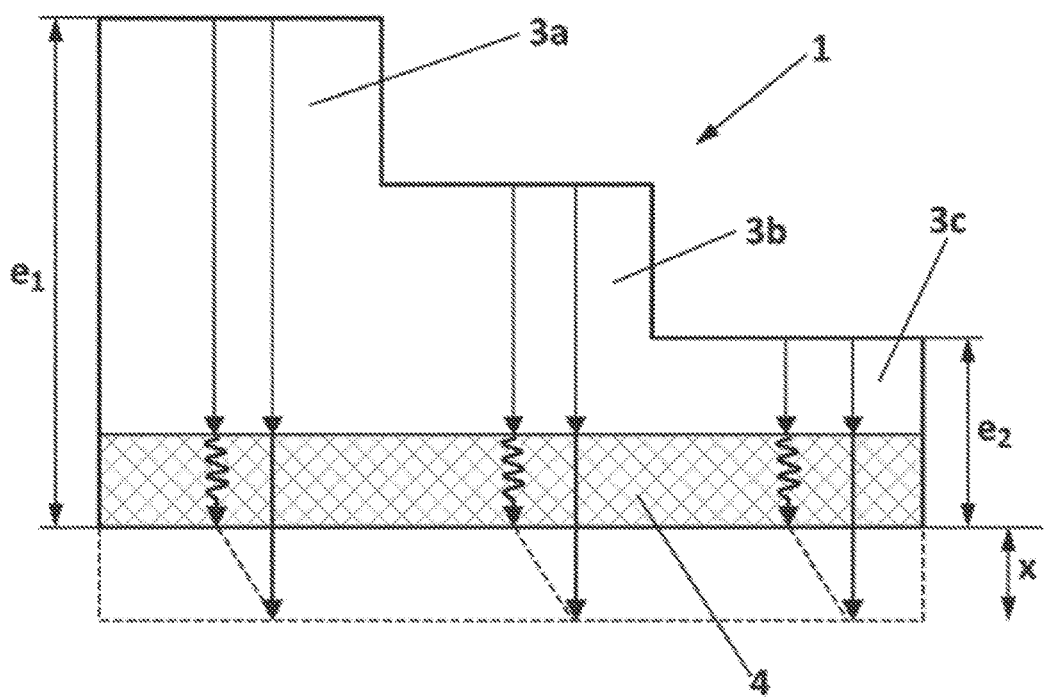
FIG. 2 is an illustration of a schematic representation of an ultrasound thickness measurement in a carbon fiber component (3) formed by parts with different thickness (3A,3B,3C) and incorporating a second material (4), as a copper mesh, adhesive etc. in accordance with an aspect of the present disclosure. The arrows in the figure represent the different ultrasound propagation speed for each material, and the error "X" caused in the carbon fiber thickness measurement due to the different ultrasonic speed in the second material.

The method of the present disclosure is suitable for measuring carbon fiber thickness, in any carbon fiber component (preferably, Carbon Fiber Reinforced Plastic), as shown in FIG. 2, having parts with different thickness (3A,3B,3C) and integrating at least one layer (4) of a second material, different than carbon fiber. Typically, in a wing skin cover of an aircraft, this second material is a copper mesh having a constant thickness though out the different parts of the component.

The real thickness of the thicker part (3A) and the real thickness of the thinner part (3C), are measured, with micrometer.

Figure 3:
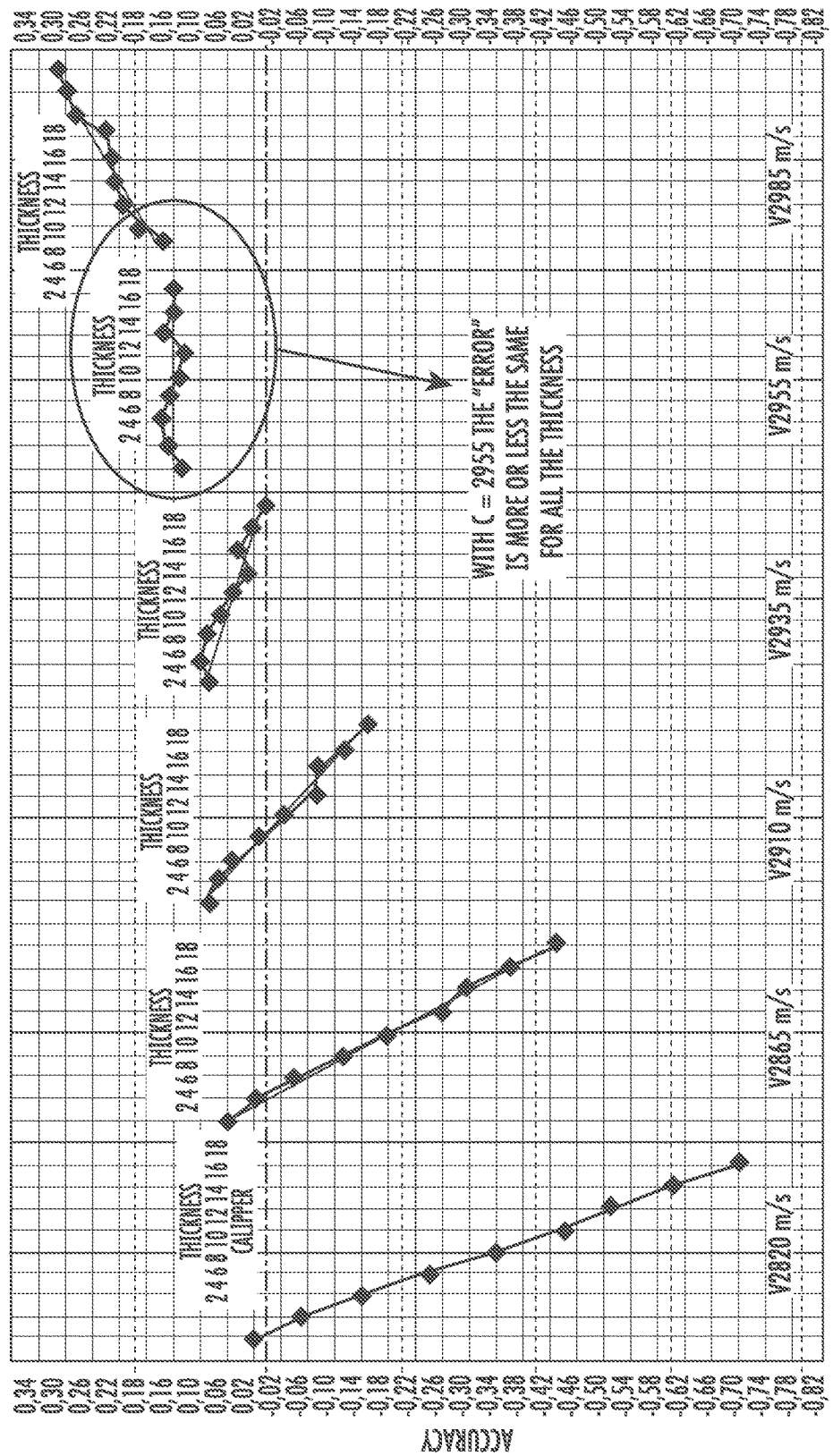
FIG. 3 is a graphic representation of the problem associated with the use of different speeds and lack of precision offered, compared with the solution that allow the use of a single speed and greater accuracy for a thickness range of 2-18 mm in accordance with an aspect of the present disclosure.

An optimum ultrasound test speed is calculated for which the difference between the measurement error at the maximum real thickness and the measurement error at the minimum real thickness of the component, is similar FIG. 3 shows the accuracy of several ultrasound speeds for a range of thickness 2-18 mm. It can be noted in the graph that an ultrasound speed of 2955 m/s is the optimum speed, since it is the one providing a similar error along the thickness of the component.

On the other hand, two time measurements are taken, one is the time that the ultrasound takes to propagate across the thicker component part, and a second one for the time that the ultrasound takes to propagate across the thinner component part.

Then, a thickness correction value (X) is calculated for each part (3A,3B,3C) of the component with different thickness. Additionally, an ultrasound test speed (Y) is also calculated from said thickness correction value, said measured times, and said measured maximum and minimum real thickness.

The process for calculating these two parameters (X),(Y) is describe below, wherein:

Y=unique ultrasound test speed
X=thickness correction value
$E_1$=measure by micrometer the real thickness of the thicker part of the component
$E_2$=measure by micrometer the real thickness of the thinner part of the component
$T_1$=time that the ultrasound takes to propagate across the thicker part of the component.
$T_2$=time that the ultrasound takes to propagate across the thinner part of the component.

Knowing that E=V·T, then:

$$E_1 + X = Y T_1$$

$$E_2 + X = Y T_2$$

$$X = Y T_1 - E_1$$

$$X = Y T_2 - E_2$$

$$Y T_1 - E_1 = Y t2 - E_2$$

$$Y T_1 - Y T_2 = E_1 - E_2$$

$$Y(T_1 - T_2) = E_1 - E_2$$

We obtain the value of the two parameters:

$$Y = (E_1 - E_2)/(T_1 - T_2)$$

$$X = (Y T_1) - E_1$$

That is, we obtain a common calculated ultrasound test speed (Y) and a thickness correction value (X) for all the parts of the component with different thickness and materials configuration.

In the case of FIG. 2, since the copper mesh thickness is constant throughout all the parts of the component, the value of (X) is the same for all the parts.

Finally, the automatic ultrasound measurement equipment is set with the calculated ultrasound test speed (Y), and using this speed he total thickness of each of the parts of the component is measured. Then, the calculated thickness correction value (X) is applied to each of the measured total thickness of each part, to obtain a corrected carbon fiber thickness for each part of the component.

FIG. 4 is a table regarding the great accuracy achieved with the method of the present disclosure, wherein it can be noted that different between the real thickness (caliper value column), and the thickness obtained by the method of the present disclosure (calculated thickness column), is less 0.52% in this particular example.

What is claimed:

1. A method for measuring carbon fiber thickness, in a carbon fiber component having parts with different thickness and integrating at least a second material, the method comprising the steps of:
   measuring with a mechanical thickness measurement device a maximum real thickness and a minimum real thickness of the carbon fiber component;
   measuring with an automatic ultrasonic equipment, a time that an ultrasound takes to propagate across the carbon fiber component part with the maximum real thickness and the carbon fiber component part with the minimum real thickness;
   calculating an optimum ultrasonic test speed and a thickness correction value for the carbon fiber component;
   wherein the thickness correction value and the optimum ultrasound test speed are determined using the time that the ultrasound takes to propagate across the carbon fiber component part with the maximum real thickness and the carbon fiber component part with minimum real thickness, and the maximum measured real thickness and the minimum measured real thickness;
   measuring a total thickness of each of the parts of the carbon fiber component, using ultrasounds with the same calculated ultrasound test speed, and
   applying the thickness correction value to each of the measuring total thickness of each part, to determine a corrected carbon fiber thickness for each part.

2. The method according to claim 1, wherein the maximum real thickness and the minimum real thickness of the carbon fiber component is measured with a micrometer.

3. The method according to claim 1, wherein the thickness of the second material is constant though out the different parts of the component.

4. The method according to claim 1, wherein the carbon fiber is a Carbon Fiber Reinforced Plastic.

5. The method according to claim 1, wherein during the step of measuring a total thickness of each of the parts of the carbon fiber component the ultrasound is generated by an automatic ultrasound measurement equipment, set at the previously calculated ultrasound test speed.

* * * * *